(12) United States Patent
Mahanthappa et al.

(10) Patent No.: US 9,221,844 B2
(45) Date of Patent: Dec. 29, 2015

(54) METAL BIS(MALONATO) BORATE MONOMERS, POLYMERS AND COPOLYMERS DERIVED THEREFROM, METHODS OF MAKING THE MONOMERS AND POLYMERS, AND ARTICLES DERIVED THEREFROM

(71) Applicant: Wisconsin Alumni Research Foundation, Madison, WI (US)

(72) Inventors: Mahesh Kalyana Mahanthappa, Madison, WI (US); Ryan Lee Weber, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 18 days.

(21) Appl. No.: 13/796,155

(22) Filed: Mar. 12, 2013

(65) Prior Publication Data

US 2014/0011970 A1    Jan. 9, 2014

Related U.S. Application Data

(60) Provisional application No. 61/667,531, filed on Jul. 3, 2012.

(51) Int. Cl.
| | |
|---|---|
| *C07F 5/04* | (2006.01) |
| *C07F 15/00* | (2006.01) |
| *C07F 1/02* | (2006.01) |
| *H01M 10/0565* | (2010.01) |
| *H01M 10/052* | (2010.01) |

(52) U.S. Cl.
CPC ... *C07F 5/04* (2013.01); *C07F 1/02* (2013.01); *C07F 15/0046* (2013.01); *H01M 10/0565* (2013.01); *H01M 10/052* (2013.01); *H01M 2300/0082* (2013.01)

(58) Field of Classification Search
CPC ........................................................ C07F 5/04
USPC ................................................. 558/288, 290
See application file for complete search history.

(56) References Cited

U.S. PATENT DOCUMENTS 7,527,899 B2 *    5/2009    Angell et al. ................. 429/303
2003/0023001 A1    1/2003    Kerr et al.

OTHER PUBLICATIONS

Driscoll et al.; "Polyelectrolyte Membranes Containing Lithium Malonato(difluoro)borate for Lithium-Ion Systems"; ESC Trans. 33(23); pp. 33-53; (2011).
Sun et al.; "New Single Ion Conductors ("polyBOP" and analogs) for Rechargeable Lithium Batteries"; Solid State Ionics; 175; pp. 743-746; (2004).
Sun et al.; "Network Single Ion Conductors Based on Comb-Branched Polyepoxide Ethers and Lithium Bis (allylmalonato)borate"; Macromolecules; 37(14); pp. 5133-5135; (2004).
Sun et al.; "Synthesis and Characterization of Network Single Ion Conductors Based on Comb-Branched Polyepoxide Ethers and Lithium Bis(allylmalonato)borate"; Macromolecules; 39; pp. 362-372; (2006).
Sun et al.; "New Gel Polyelectrolytes for Rechargeable Lithium Batteries"; Solid State Ionics; 175; pp. 713-716; (2004).
Xu et al.; "Preparation and Characterization of Novel "polyMOB" Polyanionic Solid Electrolytes with Weak Coulomb Traps"; Solid State Ionics; 147; pp. 295-301; (2002).
Xu et al.; "Polymer Electrolytes From Plasticized PolyMOBs and Their Gel Forms"; Electrochimica Acta; 48; pp. 2029-2035; (2003).
Xu et al.; "LiBOB and Its Derivatives: Weakly Coordinating Anions, and the Exceptional Conductivity of Their Nonaqueous Solutions"; Electrochemical and Solid-State Letters; 4(1); pp. E1-E4; (2001).
Xu et al.; "Novel Polyanionic Solid Electrolytes With Weak Coulomb Traps and Controllable Caps and Spacers"; Chem. Mater.; 14; pp. 401-409; (2002).
Yang et al.; "Six-Membered-Ring Malonatoborate-Based Lithium Salts as Electrolytes for Lithium Ion Batteries"; ECS Trans.; 33(39); pp. 57-69; (2011).
Sun et al.; "Synthesis and Characterization of Network Type Single Ion Conductors"; Macromolecules; 37; pp. 2219-2227; (2004).

* cited by examiner

*Primary Examiner* — Nicole M Buie-Hatcher
(74) *Attorney, Agent, or Firm* — Cantor Colburn LLP

(57) ABSTRACT

Disclosed herein are novel metal bis(malonato)borate monomers and polymers formed by polymerizing the monomers. The monomers and the polymers have conductive properties, making them particularly useful in applications requiring materials with conductive properties. When the metal is lithium, the polymers are particularly well suited for use in lithium ion batteries.

14 Claims, 3 Drawing Sheets

METAL BIS(MALONATO) BORATE MONOMERS, POLYMERS AND COPOLYMERS DERIVED THEREFROM, METHODS OF MAKING THE MONOMERS AND POLYMERS, AND ARTICLES DERIVED THEREFROM

CROSS-REFERENCE TO RELATED APPLICATION

This application claims priority to U.S. Provisional Application 61/667,531 filed on Jul. 3, 2012, which is incorporated herein by reference in its entirety.

FIELD OF THE DISCLOSURE

The present disclosure is related to metal bis(malonato) borate monomers and polymers formed from polymerization of the monomers. The polymers are particularly useful as polymeric ion conductors for use as polymer electrolytes in batteries, for example.

BACKGROUND

Electrochemical storage devices, such as batteries, can be classified into either primary or secondary batteries. Primary batteries are not designed to be recharged and are not reusable after they have been fully discharged. Secondary batteries, however, are rechargeable after they have been fully discharged. The demand for rechargeable or secondary batteries of high energy density and specific energy has, however, increased with the increasing demand for portable electronic equipment, e.g., cellular phones and laptop computers.

Among the commercially available portable rechargeable battery chemistries, Li-ion batteries provide the highest energy densities. A typical Li-ion cell consists of a lithiated cobalt oxide, lithiated nickel oxide or lithiated manganese oxide based composite cathode, a carbon-based anode, and a lithium ion containing liquid electrolyte. A modification of the Li-ion battery is the lithium-polymer battery in which a polymer or gel electrolyte, e.g., a poly(ethylene glycol) (PEG) electrolyte containing lithium salt, is used in place of a liquid electrolyte. Lithium polymer electrolytes are the electrolyte of choice over Li-ion containing liquid electrolyte in portable electronic applications because the lithium polymer battery can be processed into a thin sheet whereas Li-ion batteries require a container for holding the liquid electrolyte.

A disadvantage of the polymer-gel electrolytes currently used in Li-ion batteries is that they exhibit transference numbers on the order of about 0.2-0.4, much less than unity. By optimizing the transference number of the electrolyte, the formation of charge gradients in an electrochemical cell can be reduced, leading to a reduction in energy losses and increased efficiency. Polymeric lithium single ion conductors, defined as polymers in which anionic moieties are fixed in the polymer backbone with free or loosely bound lithium ions, are expected to produce transference numbers closer to unity by virtue of their structure in which lithium ions are free to move along the polymer backbone. However, reports of the successful synthesis of such materials are rare.

What is needed are new monomers that can be polymerized to produce conductive polymers suitable for use in applications such as lithium ion batteries.

BRIEF SUMMARY

In one aspect, included herein is a metal bis(malonato) borate monomer having the formula I

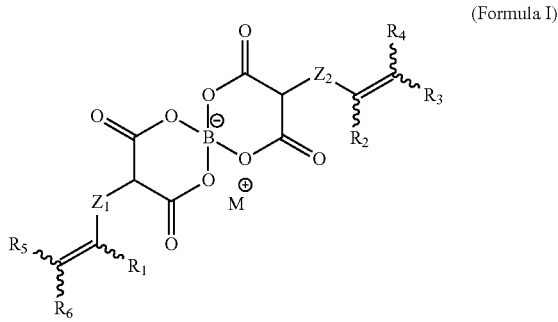

(Formula I)

wherein

M is $Li^+$, $Mg^{+2}$, $Zn^{2+}$, $Na^+$, $K^+$, $NR_4^+$ wherein R is alkyl or branched alkyl having 1 to 4 carbon atoms optionally substituted with —CN, —Cl, —F, or a combination thereof;

$Z_1$ and $Z_2$ are the same or different, and are straight-chain or branched alkylene, alkyleneoxy, alkylenoyl, alkylenoxycarbonyl, or alkylenethio having 2 to 30 carbon atoms optionally substituted with —CN or —F, alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F, alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F, or arylene having 6 to 10 carbon atoms optionally substituted with 1 to 3 straight or branched chain alkyl groups having 1 to 6 carbon atoms, —CN, or —F; and each of $R_1$, $R_2$, $R_3$, $R_4$, $R_5$ and $R_6$ are the same or different and are H, straight-chain alkyl having 1 to 12 carbon atoms, optionally substituted with —CN, —F, or an alkenyl group having 2 to 8 carbon atoms, or aryl having 6 to 10 carbon atoms optionally substituted with 1 to 3 straight or branched chain alkyl groups having 1 to 8 carbon atoms, —CN, or —F.

Also included herein is a surface having the monomer of formula I grafted thereon.

In another aspect, included herein is a polymer comprising a unit of the formula VIII

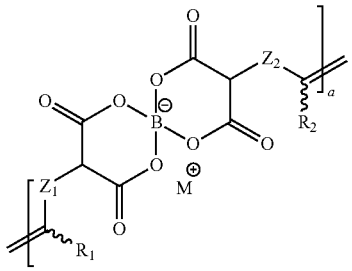

(Formula VIII)

wherein a is 10 to 300;

M is $Li^+$, $Mg^{+2}$, $Zn^{2+}$, $Na^+$, $K^+$, $NR_4^+$ wherein R is alkyl or branched alkyl having 1 to 4 carbon atoms optionally substituted with —CN, —Cl, —F, or a combination thereof;

$Z_1$ and $Z_2$ are the same or different, and are straight-chain or branched alkylene, alkyleneoxy, alkylenoyl, alkylenoxycarbonyl, or alkylenethio having 2 to 30 carbon atoms, optionally substituted with —N or —F, alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F, alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F, or arylene having 6 to 10 carbon atoms, optionally substituted with 1 to 3 straight or branched chain alkyl groups having 1 to 6 carbon atoms, —CN, or —F; and each of $R_1$ and $R_2$ are the same or different and are H, straight-chain alkyl having 1 to 12 carbon atoms, optionally substituted with —CN, —F, or an alkenyl group having 2 to 8 carbon atoms, or aryl having 6 to 10 carbon atoms, optionally substituted with 1 to 3 straight or branched chain alkyl groups having 1 to 8 carbon atoms, —CN, or —F.

In yet another aspect, included herein is a polymer having a unit of the formula

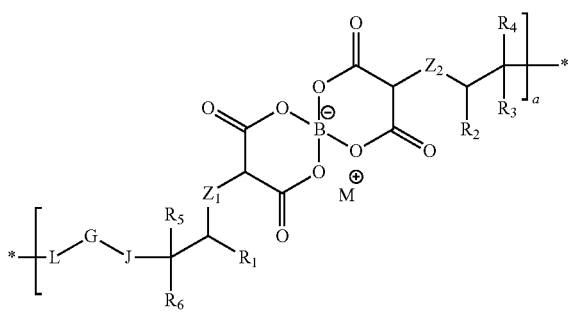

wherein
a is 2 to 300;
G is a single bond, a double bond, —O—, —S—, —NR—, —PR—, P(O)(R)—, —C(O)—, or a hydrocarbyl group having from 1 to 60 carbon atoms and a valency of q, wherein R is selected from hydrogen, a straight-chain or branched alkyl, alkoxy, or alkylthio having 1 to 8 carbon atoms, or aryl having 6 to 10 carbon atoms, optionally substituted with 1 to 3 straight or branched chain alkyl groups having 1 to 8 carbon atoms, CN, or F, wherein q is 2 to 12, specifically 2 to 8;
L and J are a sulfide, amine, phosphine, or a silane,
M is $Li^+$, $Mg^{+2}$, $Zn^{2+}$, $Na^+$, $K^+$, $NR_4^+$ wherein R is alkyl or branched alkyl having 1 to 4 carbon atoms optionally substituted with —CN, —F, —Cl, or a combination thereof;
$Z_1$ and $Z_2$ are the same or different, and are straight-chain or branched alkylene, alkyleneoxy, alkylenoyl, alkylenoxycarbonyl, or alkylenethio having 2 to 30 carbon atoms, optionally substituted with —CN or —F, alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F, alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F, or arylene having 6 to 10 carbon atoms, optionally substituted with 1 to 3 straight or branched chain alkyl groups having 1 to 6 carbon atoms, —CN, or —F; and each of $R_1$, $R_2$, $R_3$, $R_4$, $R_5$ and $R_6$ are the same or different and are H, straight-chain alkyl having 1 to 12 carbon atoms, optionally substituted with —CN, —F, or an alkenyl group having 2 to 8 carbon atoms, or aryl having 6 to 10 carbon atoms, optionally substituted with 1 to 3 straight or branched chain alkyl groups having 1 to 8 carbon atoms, —CN, or —F.

In another aspect, included is a lithium ion battery comprising a polymer of the formula

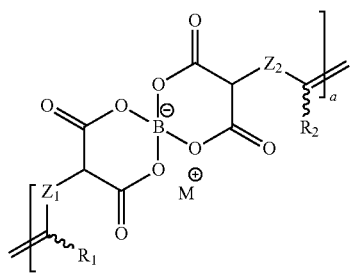

(Formula VIII)

wherein
a is 10 to 300;
M is $Li^+$;
$Z_1$ and $Z_2$ are the same or different, and are straight-chain or branched alkylene, alkyleneoxy, alkylenoyl, alkylenoxycarbonyl, or alkylenethio having 2 to 30 carbon atoms, optionally substituted with —CN or —F, alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F, alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F, or arylene having 6 to 10 carbon atoms, optionally substituted with 1 to 3 straight or branched chain alkyl groups having 1 to 6 carbon atoms, —CN, or —F; and each of $R_1$ and $R_2$ are the same or different and are H, straight-chain alkyl having 1 to 12 carbon atoms, optionally substituted with —CN, —F, or an alkenyl group having 2 to 8 carbon atoms, or aryl having 6 to 10 carbon atoms, optionally substituted with 1 to 3 straight or branched chain alkyl groups having 1 to 8 carbon atoms, —CN, or —F.

In a yet further aspect, included is a method of making a polymer having a unit of the formula VIII

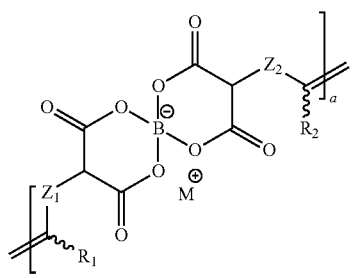

(Formula VIII)

wherein
a is 10 to 300;
M is $Li^+$, $Mg^{+2}$, $Zn^{2+}$, $Na^+$, $K^+$, $NR_4^+$ wherein R is alkyl or branched alkyl having 1 to 4 carbon atoms optionally substituted with —CN, —F, —Cl, or a combination thereof;

$Z_1$ and $Z_2$ are the same or different, and are straight-chain or branched alkylene, alkyleneoxy, alkylenoyl, alkylenoxycarbonyl, or alkylenethio having 2 to 30 carbon atoms, optionally substituted with —CN or —F, alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F, alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F, or arylene having 6 to 10 carbon atoms, optionally substituted with 1 to 3 straight or branched chain alkyl groups having 1 to 6 carbon atoms, —CN, or —F; and each of $R_1$ and $R_2$ are the same or different and are H, straight-chain alkyl having 1 to 12 carbon atoms, optionally substituted with —CN, —F or an alkenyl group having 2 to 8 carbon atoms, or aryl having 6 to 10 carbon atoms, optionally substituted with 1 to 3 straight or branched chain alkyl groups having 1 to 8 carbon atoms, —CN, or —F, the method comprising reacting a monomer of formula I with a metal catalyst in the presence of a solvent, and isolating the polymer of formula VIII.

In a still further aspect, a method of making a metal bis(malonato)borate monomer having the formula I

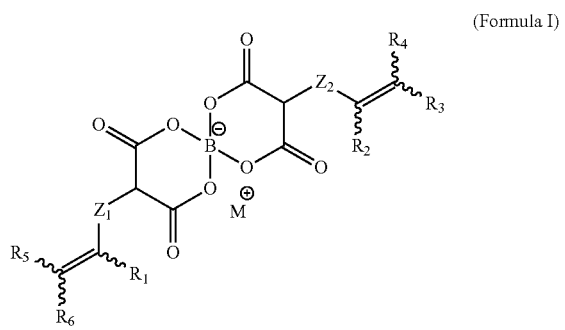

(Formula I)

M is $Li^+$, $Mg^{+2}$, $Zn^{2+}$, $Na^+$, $K^+$, $NR_4^+$ wherein R is alkyl or branched alkyl having 1 to 4 carbon atoms optionally substituted with —CN, —F, —Cl, or a combination thereof;

$Z_1$ and $Z_2$ are the same or different, and are straight-chain or branched alkylene, alkyleneoxy, alkylenoyl, alkylenoxycarbonyl, or alkylenethio having 2 to 30 carbon atoms, optionally substituted with —CN or —F, alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F, alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F, or arylene having 6 to 10 carbon atoms, optionally substituted with 1 to 3 straight or branched chain alkyl groups having 1 to 6 carbon atoms, —CN, or —F; and each of $R_1$, $R_2$, $R_3$, $R_4$, $R_5$ and $R_6$ are the same or different and are H, straight-chain alkyl having 1 to 12 carbon atoms, optionally substituted with —CN, —F or an alkenyl group having 2 to 8 carbon atoms, or aryl having 6 to 10 carbon atoms, optionally substituted with 1 to 3 straight or branched chain alkyl groups having 1 to 8 carbon atoms, —CN, or —F, the method comprising reacting a carboxylic acid of formula IV, V or a combination thereof, with a base to deprotonate an alpha carbon and produce one or more reactive alpha carbon carbanions, wherein

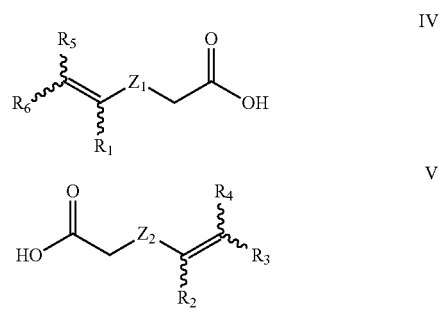

carboxylating the one or more reactive alpha carbon carbanions using carbon dioxide to produce an alpha-substituted malonic acid of formula VI, VII, or a combination thereof

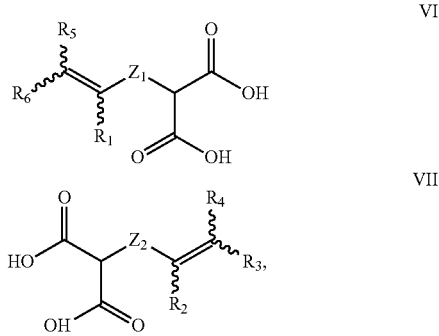

reacting the alpha-substituted malonic acid of formula VI, VII, or a combination thereof with a protecting group to form a corresponding diester, and contacting the diester with a boron-containing compound to chelate the alpha-substituted malonic acid of formula VI, VII, or a combination thereof, and produce the monomer of formula I.

Figure 1:
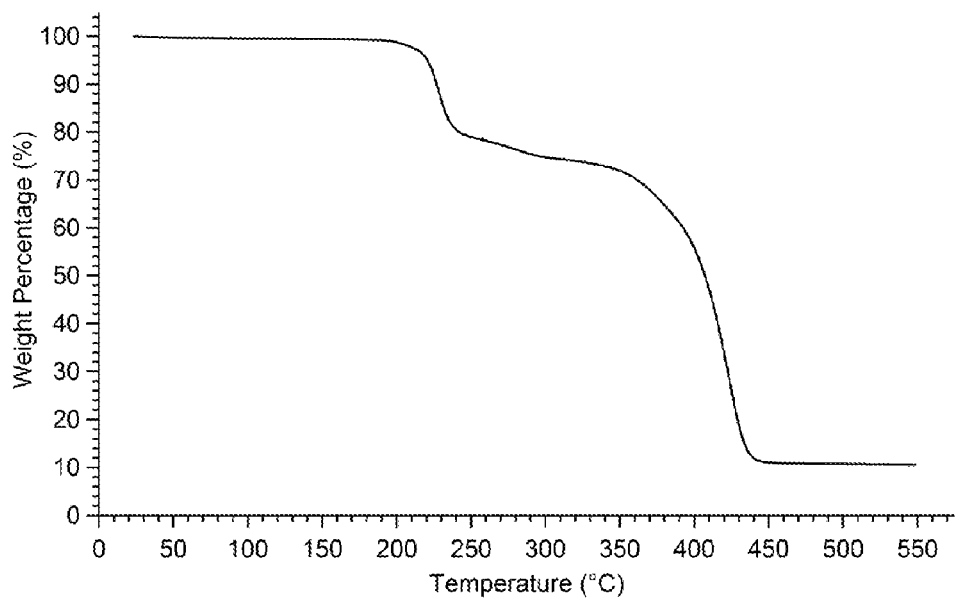
FIG. 1 shows a thermogravimetric analysis of poly(lithium bis(non-8-enyl-malonato)borate) (4) establishing the thermal stability of this polymer up to 200° C., after which two substantial weight loss waves are observed at T=235° C. and 450° C.

The above-described and other features will be appreciated and understood by those skilled in the art from the following detailed description, drawings, and appended claims.

DETAILED DESCRIPTION

Described herein are novel long-chain alkenyl-substituted metal bis(malonato)borate monomers and polymers made from polymerizing the monomers. The polymers are particularly useful as polymeric single ion conductors for lithium ions, and are expected to have transference numbers (i.e., ion transport numbers) that are favorable for use in electrochemical cells such as batteries.

In an embodiment, a metal bis(malonato)borate monomer has the formula I

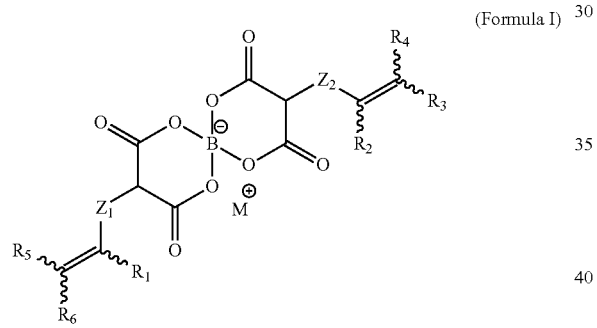

(Formula I)

wherein

M is $Li^+$, $Mg^{+2}$, $Zn^{2+}$, $Na^+$, $K^+$, $NR_4^+$ wherein R is alkyl or branched alkyl having 1 to 4 carbon atoms optionally substituted with —CN, —F, —Cl, or a combination thereof;

$Z_1$ and $Z_2$ are the same or different, and are straight-chain or branched alkylene, alkyleneoxy, alkylenoyl, alkylenoxycarbonyl, or alkylenethio having 2 to 30 carbon atoms, specifically 2 to 20 carbon atoms, and more specifically 2 to 12 carbon atoms, optionally substituted with —CN or —F, alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F, alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F, or arylene having 6 to 10 carbon atoms, optionally substituted with 1 to 3 straight or branched chain alkyl groups having 1 to 6 carbon atoms, —CN, or —F; and each of $R_1$, $R_2$, $R_3$, $R_4$, $R_5$ and $R_6$ are the same or different, and are H, straight-chain alkyl having 1 to 12, specifically 1 to 10 and more specifically 1 to 8 carbon atoms, optionally substituted with —CN, —F or an alkenyl group having 2 to 8 carbon atoms, or aryl having 6 to 10 carbon atoms, optionally substituted with 1 to 3 straight or branched chain alkyl groups having 1 to 8 carbon atoms, —CN, or —F.

In formula I, $Z_1$ and $Z_2$ are linkers between the malonate group and a double bond. In an embodiment, $Z_1$ and $Z_2$ are each a straight chain alkylene, alkyleneoxy, or alkylenethio having 2 to 20, specifically 7 to 11, and most specifically 7 carbon atoms. In an embodiment, for use as a single ion conductor at voltages of less than about 5 volts relative to $Li/Li^+$, $Z_1$ and $Z_2$ are alkylene, alkyleneoxy, alkylenoyl, alkylenoxycarbonyl, alkylenethio, or arylene, having 2 to 18 carbon atoms. For use as a single ion conductor at voltages of about 5 volts relative to $Li/Li^+$ or higher, $Z_1$ and $Z_2$ are alkylene, alkyleneoxy, or alkylenethio.

In an embodiment, $R_1$ and $R_2$ are the same. In another embodiment, $R_3$, $R_4$, $R_5$ and $R_6$ are the same. In yet another embodiment, $R_1$ and $R_2$ are the same and $R_3$, $R_4$, $R_5$ and $R_6$ are the same. In an embodiment, $R_1$ and $R_2$ are hydrogen. In another embodiment, $R_3$, $R_4$, $R_5$ and $R_6$ are hydrogen. In yet another embodiment, $R_1$, $R_2$, $R_3$, $R_4$, $R_5$, and $R_6$ are hydrogen. In an embodiment, $R_1$, $R_2$, $R_3$, and $R_6$ are H, and $R_4$ and $R_5$ are the same, such as, for example, a monomer derived from a long chain fatty acid having a cis-olefin group, such as oleic acid.

In an embodiment, M is $Li^+$.

In a specific embodiment, the metal bis(malonato)borate monomer has the formula II:

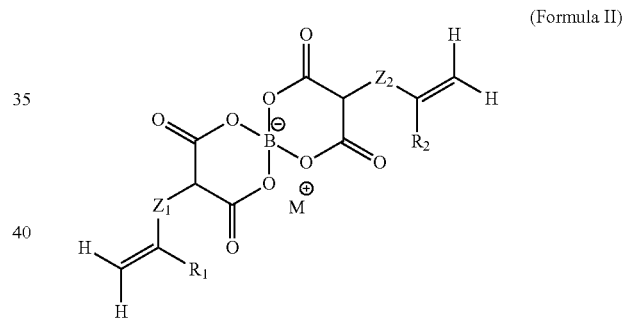

(Formula II)

wherein M, $Z_1$, $Z_2$, $R_1$ and $R_2$ are as defined above.

In a more specific embodiment, the metal bis(malonato) borate monomer has the formula III:

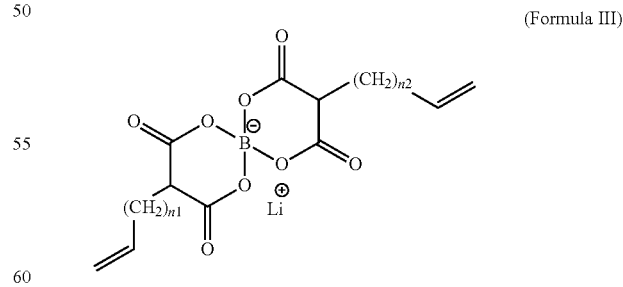

(Formula III)

wherein $n_1$ and $n_2$ are 2 to 20, specifically 2 to 12, and more specifically 7 to 12.

The metal bis(malonato)borate monomers having any of formulas I, II, and III can be prepared from widely available carboxylic acid starting materials having at least one unsaturated group. For example, the synthesis can use as a starting material a carboxylic acid that is converted to an alpha-substituted malonic acid, for example a carboxylic acid of the formulas IV, V, or a combination thereof:

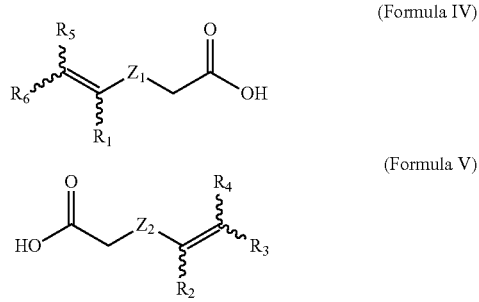

(Formula IV)

(Formula V)

wherein $Z_1$, $Z_2$, $R_1$, $R_2$, $R_3$, $R_4$, $R_5$ and $R_6$ are as defined in formula I.

The alpha carbon of the carboxylic acid can be deprotonated using a base strong enough to deprotonate an alpha carbon. Conditions for deprotonation are known in the art. Suitable bases include alkyllithiums, alkylmagnesium reagents, lithium diisopropylamide, lithium tetramethylpiperidine, dialkyamide base, sodium hydride, and potassium hydride, among other suitable strong bases. The reaction suitably occurs in an aprotic solvent, e.g., tetrahydrofuran, diethyl ether, hexamethylphosphoramide, dioxane, ethylene glycol dimethyl ether, and the like. The reaction suitably occurs at temperatures below 0° C., such as below −10° C., below −20° C., such as about −25° C.

The reactive alpha-carbon carbanion can then be carboxylated, for example by contacting with carbon dioxide or a synthesis equivalent thereof to prepare an alpha-substituted malonic acid of the formulas VI, VII, or a combination thereof:

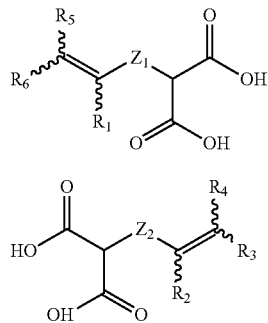

VI

VII wherein $Z_1$, $Z_2$, $R_1$, $R_2$, $R_3$, $R_4$, $R_5$ and $R_6$ are as defined in formula I. The substituents are selected to yield the desired products I, II, or III as described above. For example, a specific starting carboxylic acid V is 10-undecenoic acid, which yields the alpha-substituted malonic acid 2-(non-8-en-1-yl) malonic acid.

To form the metal bis(malonato)borate monomer the alpha-substituted malonic acid can first be reacted to yield an activating group, for example, a group selected from among trimethylsilyl, triethylsilyl, tert-butyl-dimethylsilyl, triisopropylsilyl, and the like to form the corresponding diester. Conditions for such reactions are known.

The alpha-substituted malonate diester is thereafter contacted with a boron-containing compound to chelate boron with the alpha-substituted malonate to form the metal bis(malonato)borate monomer of structures I, II, or III. The boron-containing compounds can be a boron salt, for example a tetrafluoroborate salt charge balanced with any of the cations M identified above in connection with structures (I) to (III); or a boron salt of the formula $[B(OR)_4]^-$ (wherein R is a $C_{1-6}$ alkyl, e.g., methyl, ethyl, isopropyl, n-propyl, n-butyl), s-butyl, or t-butyl) charge balanced with any of the cations M identified above in connection with structures (I) to (III). Other cations can be used, but the charge balancing cation advantageously provides the cation M in formulas I, II, or III.

Two equivalents of the activated alpha-substituted malonate ester react with one equivalent of the boron containing compound to yield a bis(malonato) chelate of boron of the structure (I), (II), or III. Conditions for the reaction depend on the particular alpha-substituted malonate diester used, the particular boron-containing compound used, and like considerations. For example, reaction can be conducted in an aprotic solvent at a temperature of 25 to 75° C., for a period of 4 to 200 hours.

The metal bis(malonato)borate monomers I, II, and III are useful as conductive molecules as described above. Alternatively, the unsaturated groups in monomers I, II, or III can be used for further reaction.

Thus, in an embodiment, the monomers can be polymerized to form polymers (including heteropolymers and copolymers) by a variety of polymerization methods.

For example, when at least one of $R_3$ and $R_4$, and at least one of $R_5$ and $R_6$ is hydrogen, one or more the of metal bis(malonato)borate monomers can polymerized via acyclic diene metathesis (ADMET). For example, when each of $R_3$, $R_4$, $R_5$, and $R_6$ is hydrogen an ADMET polymer can be produced, represented by Formula VIII:

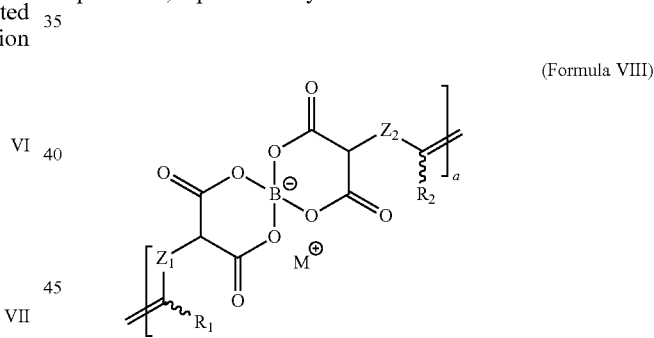

(Formula VIII)

wherein M, $Z_1$, $Z_2$, $R_1$ and $R_2$ are as defined formulas I, II, and III, and wherein a is about 10 to about 300, specifically about 50 to about 100. In an exemplary embodiment, the number average molecular weight of the polymers is about 5 to about 100 kg/mol, specifically 30 to 52 kg/mol, number average molecular weight. Molecular weights can be measured against poly(ethylene oxide) standards, using size exclusion chromatography. In an embodiment, the polydispersity index against poly(ethylene oxide) standards is $M_w/M_n$ of about 1.5-2.0.

In an embodiment, the polymer is a homopolymer in which each $Z_1$, $Z_2$, $R_1$ and $R_2$ is the same. In another embodiment, the polymer is a heteropolymer comprising 2, 3, 4, or more different metal bis(malonato)borate monomers.

Conditions for ADMET polymerization are known, and are conducted in the presence of metal catalysts, for example ruthenium catalysts of the general structure $(L)(L')(X)_2$ Ru=CRR' such as Grubbs first generation catalyst (benzylidene-bis(tricyclohexylphosphine)dichlororuthenium), Grubbs second generation catalyst (benzylidene[1,3-bis(2,4,6-trimethylphenyl)-2-imidazolidinylidene]dichloro(tricyclohexylphosphine)ruthenium), and the like. Reaction conditions can vary, for example polymerization can be conducted in an aprotic, anhydrous solvent such as propylene carbonate under vacuum.

In still another embodiment, a metal bis(malonato)borate monomer of formula I, II or III is polymerized with a comonomer comprising at least two groups reactive with the unsaturated groups of the monomer of formulas I, II, or III by addition polymerization to form a copolymer. Such comonomers can be represented schematically by formula IX $$G\text{-}(X)_n \quad \text{(Formula IX)}$$

wherein

G is a single bond, a double bond, —O—, —S—, —NR—, —PR—, P(O)(R)—, —C(O)—, or a hydrocarbyl group having from 1 to 60 carbon atoms and a valency of q, wherein R is selected from straight-chain or branched alkyl, alkoxy, or alkylthio having 1 to 8 carbon atoms, or aryl having 6 to 10 carbon atoms, optionally substituted with 1 to 3 straight or branched chain alkyl groups having 1 to 8 carbon atoms, CN, or F, and wherein q is 2 to 12, specifically 2 to 8;

n is 2 to 12, 2 to 6, to 4, or to 3; and

X is the same or different and is a group reactive with the unsaturated group of borate monomer I, II, or III.

There are no particular limitations with respect to G, except that any substituents do not substantially interfere with polymerization. G can be a hydrocarbon having 1 to 45 carbon atoms, 1 to 30 carbon atoms, or 1 to 18 carbon atoms. G can be aliphatic, unsaturated, aromatic, or a combination thereof, straight chain, branched, or cyclic, and can optionally contain heteroatoms, for example halogen, N, O, S, P, Si, or a combination thereof, for example 0 to 40 or 1 to 12 or 1 to 4 heteroatoms. G groups containing an Si—O, P—O, P—N, C—Si, C—O, C—S, S—P, or S—O bond are specifically contemplated. In an embodiment, G is —(OSiR$_2$)$_m$—, wherein m is 1 to 20.

In an embodiment, G is

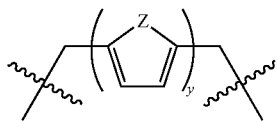

wherein Z is S or O, and y is 1-20, specifically 5 to 15, and more specifically 10.

X can be any group reactive with the unsaturated group of borate monomer I, II, or III. For example, each X can be a thiol group HS—, an alkenyl group, a reactive amine of the formula R$_7$HN—, a reactive silane of the formula R$_7$R$_8$HSi—, a reactive phosphine of the formula R$_7$HP— wherein each R$_7$ and R$_8$ are the same or different and are selected from hydrogen, straight-chain or branched alkyl, alkoxy, or alkylthio having 1 to 8 carbon atoms, or aryl having 6 to 10 carbon atoms, optionally substituted with 1 to 3 straight or branched chain alkyl groups having 1 to 8 carbon atoms, —CN, or —F. In an embodiment, each X is the same.

Such copolymerizations can be represented schematically as follows, wherein n is 2, and each X is different, and is a reactive group of the formulas -LH and -JH:

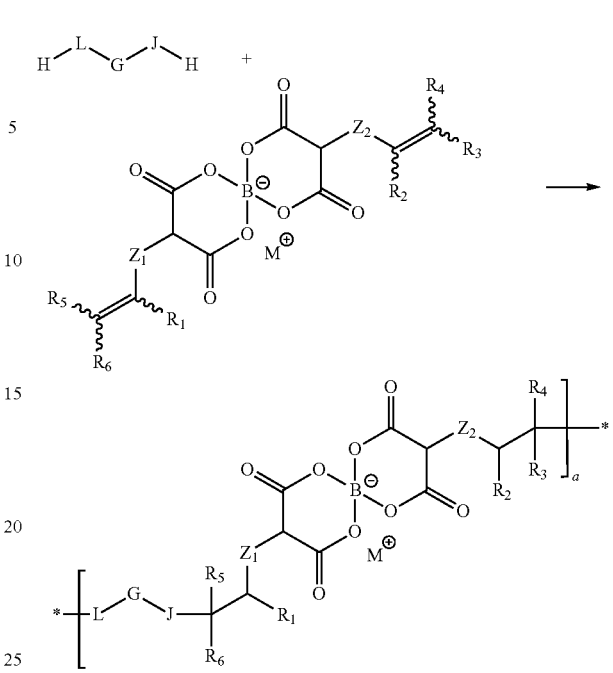

wherein M, R$_1$, R$_2$, Z$_1$ and Z$_2$, X, Y and G are as defined above, and L and J are a sulfide, a silane, a phosphine, an amine, or the like, and a is 2 to about 300, specifically about 4 to about 100, or about 10 to about 50. As shown, when n is 2, a linear polymer results. When n is 3 or greater, a crosslinked polymer results. A combination of different comonomers can be used, for example a combination of monomers wherein n is 2 and n is 3, 4, or more.

Conditions for addition polymerization are known, and depend on the particular reactive group X. For example, in a thiol-ene polymerization reaction, each X is a thiol group —SH. Copolymerization occurs in the presence of a radical initiator such as azobisisobutyronitrile (AIBN), azobiscyclohexylcarbonitrile (V-40), benzoyl peroxide, lauroyl peroxide (Luperox™), UV light (λ≤400 nm), 2,2-dimethoxyphenyl acetophenone (Irgacure® 651), and the like, in a solvent such as benzene, acetone, ethanol, 1,2-dichloroethane, propylene carbonate, dimethyl carbonate, diethyl carbonate, ethylene carbonate, butanone, ethylene glycol dimethyl ether, or DMF at a temperature of 25 to 140° C. to produce the polymer.

In a hydrosilation polymerization, each X is R$_7$R$_8$HSi—, and G is a hydrocarbyl, which includes a silicone. Copolymerization occurs in the presence of a transition metal (e.g., platinum or rhodium) catalyst in an aprotic solvent such as benzene, acetone, or tetrahydrofuran (THF) at a temperature of 25 to 140° C. to produce the polymer.

In a phosphinylation polymerization, each X and Y are R$_9$HP— and G is a hydrocarbyl, which includes a silicone. Copolymerization occurs in the presence of a radical initiator such as AIBN, V-40, benzoyl peroxide, lauroyl peroxide (Luperox™), UV light (λ≤400 nm), 2,2-dimethoxyphenyl acetophenone (Irgacure® 651), and the like, in a solvent such as benzene, acetone, ethanol, 1,2-dichloroethane, propylene carbonate, dimethyl carbonate, diethyl carbonate, ethylene carbonate, butanone, ethylene glycol dimethyl ether, or DMF at a temperature of 25 to 140° C. to produce the polymer.

In still another embodiment, a long-chain alkenyl-substituted metal bis(malonato)borate monomer I, II, or III is grafted onto a surface, such as a carbon, silicon, germanium, tin, or metal oxide surface. Grafting procedures include photochemical grafting as well as chemical grafting. The surfaces grafted with the monomers can be used as the anode or the cathode of an electrochemical cell, absorbing the stresses encountered when the electrode is charged or discharged, a process that typically involves a large volume change. Photochemical grafting can be performed by contacting the surface with the long-chain alkenyl-substituted metal bis(malonato)borate monomer in the presence or the absence of a solvent, and exposing the surface to ultraviolet light, such as 254 nm light. The particular wavelength of the UV light can vary and will depend upon the identity of the linker precursor and the surface. In some embodiments, the UV light is mid-UV light having a wavelength between 300 nm and 200 nm. In some such embodiments, the UV light is UV light at 254 nm. In other embodiments, the UV light is near-UV light having a wavelength between 400 nm and 300 nm.

In another embodiment, chemical grafting can be performed by contacting the surface with the long-chain alkenyl-substituted metal bis(malonato)borate monomer in the presence or the absence of a solvent, and a metal catalyst such as platinum(0)-1,3-divinyl-1,1,3,3-tetramethyldisiloxane (Karstedt's catalyst) or chloroplatinic acid (Speier's catalyst) to graft the monomer to a Si—H terminated surface.

In yet another embodiment, chemical grafting to a surface can also be performed by contacting the surface with the long-chain alkenyl-substituted metal bis(malonato)borate monomer in the presence or the absence of a solvent using a thermal initiator such as, for example, AIBN, benzoxyl peroxide, or lauroyl peroxide (Luperox™) in the temperature range 22-200° C., specifically 50-150° C.

When the surface is a carbon, silicon, germanium, or tin surface, the surface is an unoxidized surface that can be prepared by hydrogen-terminating the carbon, silicon or germanium surface. For example, a silicon surface can be etched with HF to form an H-terminated silicon surface. A carbon surface can be prepared by exposure to atomic hydrogen, which removes oxidized sites and provides surface atoms that are terminated with hydrogen. In an embodiment, the long-chain alkenyl-substituted metal bis(malonato)borate monomer is bonded directly to the surface of the substrate through reaction of an alkene in the monomer, either by photochemical or chemical grafting.

In an embodiment, the carbon surface is a carbon nanotube such as a single-walled or multi-walled carbon nanotube or a graphite sheet.

In an embodiment, the metal oxide surface is in the form of a nanoparticle, such as particles of mixed metal oxides. Advantageously, the use of metal oxide particles provides a high surface area compared to a flat surface.

A lithium single-ion conductive polymer as described herein, such as a polymer of formula VIII wherein M is Li$^+$, is particularly useful in lithium ion battery applications. As used herein, a lithium ion battery is an electrochemical cell comprising, in electrical communication, an anode, a cathode and an electrolyte, wherein the lithium ion battery comprises a lithium single-ion conductive polymer as described herein.

The anode contains an active material that can be oxidized; the cathode contains or consumes an active material that can be reduced. The anode active material is capable of reducing the cathode active material. In an embodiment, the anode comprises an active substance layer comprised of a carbonaceous material capable of absorption and desorption of lithium ions such as graphite. Nonlimiting examples of suitable anode active materials include carbonaceous materials such as artificial graphite, natural graphite, graphitizable carbon fiber, graphitizable mesocarbon microbeads, amorphous carbon, and the like. The anode active material can include an elementary metal substance capable of alloying with lithium, or a composite of a metal material and a carbonaceous material. Nonlimiting examples of metals capable of alloying with lithium include Al, Si, Sn, Pb, Zn, Bi, In, Mg, Ga, Cd, and the like. The anode active material can alternatively comprise a lithium metal foil. The cathode comprises an active substance layer comprised of a metal oxide complex containing lithium capable of absorption and desorption of lithium ions such as $LiCoO_2$, $LiFeO_2$, $LiNi_nCo_{1-n}O_2$, $LiMn_2O_4$, lithium nickel manganese cobalt oxide ($LiNi_{1-y-z}Mn_yCo_zO_2$), or lithium nickel manganese oxide ($LiNi_{1-y}Mn_yO_2$), which is coated on aluminum or stainless steel, for example.

In an embodiment, the cathode comprises a binder which aids in deposition and or retention of the cathode active material. A lithium single-ion conductive polymer as described herein can be used as a cathode binder. In another embodiment, a cathode comprises a cathode passivation layer which prevents direct contact between the cathode and the electrolyte, e.g., a non-aqueous electrolyte. A lithium single-ion conductive polymer as described herein can be used as a cathode passivation layer.

In an embodiment, an electrochemical cell comprises a separator layer disposed between the anode and the cathode. The separator layer allows lithium ions to pass through, and can comprise a porous material such as polyethylene, polypropylene, poly(ethylene oxide) or a lithium single-ion conductive polymer as disclosed herein.

When a battery is used as an electrical energy source in a device, electrical contact is made to the anode and the cathode, allowing electrons to flow through the device and permitting the respective oxidation and reduction reactions to occur to provide electrical power. An electrolyte in contact with the anode and the cathode contains ions that flow through the optional separator between the electrodes to maintain charge balance throughout the battery during discharge.

In an embodiment, the electrolyte is a nonaqueous electrolyte comprising a solvent and a lithium-containing solute. Solvents include, for example, carbonates such as ethylene carbonate, propylene carbonate, butylene carbonate, vinylene carbonate, dimethyl carbonate, methyl ethyl carbonate, dipropyl carbonate, ethylpropyl carbonate, or diethyl carbonate, halogen-substituted carbonates, and mixtures thereof. Also useful is a mixed solvent of a carbonate and an ether solvent such as 1,2-dimethoxyethane or 1,2-diethoxyethane. Examples of electrolyte solutes include $LiPF_6$, $LiBF_4$, $LiCF_3SO_3$, $LiN(CF_3SO_2)_2$, $LiN(C_2F_5SO_2)_2$, $LiN(CF_3SO_2)(C_4F_9SO_2)$, $LiC(CF_3SO_2)_3$, $LiC(C_2F_5SO_2)_3$, and mixtures thereof. In one embodiment, the electrolyte is a polymer of Formula VIII dissolved in a non-aqueous solvent.

Other applicable electrolytes include a gelled polymer electrolyte comprised of a nonaqueous electrolyte solution impregnated into a polymer such as polyvinylidene fluoride, polyacrylonitrile, polyethylene oxide, polyvinyl chloride, polyacrylate, polyvinylidene fluoride hexafluoropropylene.

In another embodiment, a gelled polymer electrolyte further comprises a lithium single-ion conductive polymer as disclosed herein.

In another embodiment, the electrolyte is a non-volatile polymer electrolyte comprising a lithium single-ion conductive polymer with or without a non-aqueous solvent as described herein.

The invention is further illustrated by the following non-limiting examples.

EXAMPLES

Materials: All chemicals were purchased from Sigma-Aldrich Chemical Company (Milwaukee, Wis.) and were used as received unless otherwise noted. Diisopropylamine, hexamethylphosphoramide (HMPA), $CH_3CN$, and propylene carbonate were distilled from $CaH_2$ followed by degassing with three freeze-thaw cycles, then stored under nitrogen. Acetone was distilled from Drierite™ ($CaSO_4$(s)) and degassed by three freeze-thaw cycles, and it was stored under nitrogen. 2.5 M n-butyllithium in hexanes was titrated against diphenylacetic acid in tetrahydrofuran (THF). Dry pentane was obtained by stirring over anhydrous $MgSO_4$(s) followed by filtration. Anhydrous lithium tetrafluoroborate ($LiBF_4$) was obtained by stirring powder under vacuum at 85° C. overnight then stored under nitrogen. 1,6-Hexanedithiol and trimethylpropane tris(3-mercaptopropionate) were dried by passing through a plug of activated silica gel. Anhydrous and anaerobic THF and toluene were obtained by sparging analytical grade solvent with $N_2$(g) for 30 minutes followed by cycling through a column of activated alumina in a Vacuum Atmospheres Solvent purification system for at least 12 hr.

NMR Spectroscopy: $^1H$ and $^{13}C$ NMR spectra were recorded on Varian Inova 500, Varian Mercury Plus, or Bruker AC+300 spectrometers and were referenced relative to the residual protiated solvent peak.

Mass Spectrometry: Mass Spectrometry was performed using a Waters (Micromass) LCT® electrospray ionization time-of-flight mass spectrometer operating in negative ion detection mode. Samples dissolved in methanol were sprayed with a sample cone voltage of 20 V.

Thermogravimetric Analysis: The thermal stability of poly (lithium bis(non-8-enylmalonato)borate) was measured on a TA Instruments Q500 Thermogravimetric Analyzer using a ramp rate of 10° C./min with under an $N_2$(g) purge (50 mL/min) over a temperature range 25-500° C.

Example 1

Synthesis of Lithium bis(non-8-enyl-malonato)borate (3) Monomer

Lithium bis(non-8-enyl-malonato)borate (3) monomer was prepared according to the following reaction sequence:

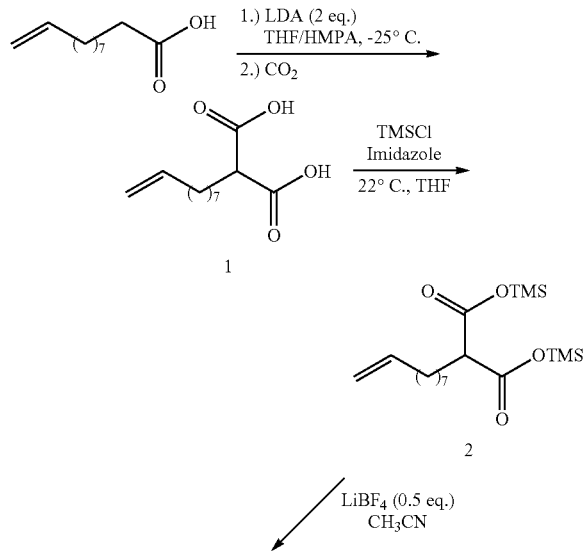

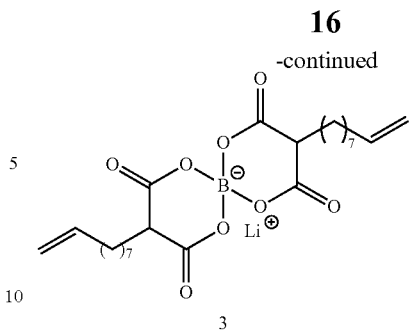

Synthesis of non-8-enyl-malonic acid (1): An oven-dried 500 mL 2-neck flask equipped with magnetic stirbar and addition funnel was charged with diisopropylamine (12.8 mL, 91.1 mmol) and THF (180 mL) under nitrogen. The solution was chilled to −25° C. in a dry ice/water/ethanol bath, and n-butyllithium (34 mL of a 2.65 M solution in hexanes, 89.0 mmol) was added dropwise via addition funnel. The solution was stirred for 30 min, after which a degassed solution of undecenoic acid (8.0 g, 43.4 mmol) in THF (44 mL) was added dropwise via addition funnel, causing the solution to become turbid. HMPA (8 mL, 43.4 mmol) was added via addition funnel. The cooling bath was then removed to allow the solution to warm to room temperature over 30 min, during which time the solution turned clear and yellow. The solution was cooled again to −25° C. A second 500 mL 2-neck flask under $N_2$(g) purge was charged with $CO_2$(s) (200 g, 4.5 mol) and chilled to −25° C. The enolate solution was cannula transferred onto the $CO_2$(s) under $N_2$(g) purge, causing the solution to become clear and colorless. The solution was stirred at −25° C. for 30 minutes then the cooling bath was removed and stirring continued at 22° C. overnight, during which time the reaction gelled. The reaction was quenched by the addition of 10% HCl (aq) (100 mL), causing two layers to form. This biphasic mixture was transferred to a reparatory funnel, and the organic layer was collected and the aqueous layer was extracted with ether (3×75 mL). The combined organic layers were then washed successively with 2M HCl (aq) (3×50 mL), water (75 mL), saturated NaCl (aq) (75 mL), and then dried over anhydrous $MgSO_4$ (s). The solvent was removed on a rotary evaporator to yield 9.5 g of white solid. The crude product was recrystallized from heptane to yield white crystals. Yield: 9.07 g (92% yield). $^1H$ NMR (300 MHz, DMSO-$d_6$, 22° C.): δ (ppm) 12.62 (s, 2H, CH $(COOH)_2$), 5.78 (ddt, $J_{H-H}{}^3$=17.0, 10.3, 6.8 Hz, 1H, $CH_2$=$CHCH_2$), 4.98 (ddt, $J_{H-H}{}^3$=17.2, 1.6 Hz, $J_{H-H}{}^3$2.2 Hz, 1H, $CH_2$=$CHCH_2$), 4.93 (ddt, $J_{H-H}{}^3$=10.2, 1.2 Hz, $J_{H-H}{}^2$=2.3 Hz, 1H, $CH_2$=$CHCH_2$), 3.17 (t, $J_{H-H}{}^3$=7.5 Hz, 1H, $CH(COOH)_2$), 2.00 (dt, $J_{H-H}{}^3$=7.0, 6.8 Hz, 2H, $CH_2$=$CHCH_2$), 1.73-1.63 (m, 2H, $CH_2CH(COOH)_2$), 1.40-1.16 (m, 10H, $CH_2$=$CHCH_2(CH_2)5CH_2CH(COOH)_2$). $^{13}C$ NMR (75 MHz, DMSO-$d_6$, 22° C.): δ (ppm) 170.90, 138.82, 114.64, 51.60, 33.18, 28.69, 28.64, 28.41, 28.24, 26.79. ESI-MS: calcd. for $C_{12}H_{20}O_4Na$ [M+Na]$^+$251.1, found 251.1.

Synthesis of non-8-enyl-malonic acid bis(trimethylsilyl) ester (2): An oven-dried 200 mL schlenk flask was charged with a magnetic stirbar, imidazole (5.04 g, 73.58 mmol), and THF (70 mL) under nitrogen. Trimethylsilyl chloride (11.5 mL, 87.60 mmol) was added via syringe, resulting in formation of a white precipitate. A degassed solution of 1 (8.0 g, 35.04 mmol) in THF (30 mL) was cannula transferred into the reaction flask over 10 minutes. Additional THF (20 mL) was used to rinse the flask containing the monomer to ensure complete transfer of 1. The solution was stirred vigorously overnight at 22° C. Volatiles were removed under vacuum to yield a white paste. This white paste was extracted by stirring with dry pentane (60 mL), allowing the suspension to settle, and by cannula filtration into a clean Schlenk flask. The extractive work up was repeated twice more (2×35 mL), and the combined pentane washes were concentrated under vacuum to yield a clear, slightly yellow liquid. Yield: 12.2 g (93% yield).

This water-sensitive intermediate was carried on to the next step of the synthesis without further purification. $^1$H NMR (300 MHz, DMSO-$d_6$, 22° C.): δ (ppm) 5.78 (ddt, $J_{H-H}^3$=17.2, 10.2, 6.7 Hz, 1H, CH$_2$=CHCH$_2$), 4.98 (ddt, $J_{H-H}^3$=17.2, 1.6 Hz, $J_{H-H}^2$=2.2 Hz, 1H, CH$_2$=CHCH$_2$), 4.93 (ddt, $J_{H-H}^3$=10.2, 1.2 Hz, $J_{H-H}^2$=2.3 Hz, 1H, CH$_2$=CHCH$_2$), 3.35 (t, $J_{H-H}^3$=7.5 Hz, 1H, CH(COOSi(CH$_3$)$_3$)$_2$), 2.00 (dt, $J_{H-H}^3$=7.2, 6.8 Hz, 2H, CH$_2$=CHCH$_2$), 1.74-1.64 (m, 2H, CH$_2$CH(COOSi(CH$_3$)$_3$)$_2$), 1.40-1.15 (m, 10H, CH$_2$=CHCH$_2$(CH$_2$)$_5$CH$_2$CH(COOSi(CH$_3$)$_3$)$_2$), 0.24 (s, 18 H, CH(COOSi(CH$_3$)$_3$)$_2$). $^{13}$C NMR (75 MHz, DMSO-$d_6$, 22° C.): δ (ppm) 169.26, 138.72, 114.56, 53.96, 33.15, 28.50, 28.27, 28.16, 28.06, 26.39, −0.60.

Synthesis of lithium bis(non-8-enyl-malonato)borate (3): An oven-dried 100 mL Schlenk flask was charged with a magnetic stirbar and LiBF$_4$ (1.49 g, 15.89 mmol) under a nitrogen atmosphere then capped with a septum. CH$_3$CN (5 mL) was added to the flask via syringe. A degassed solution of 2 (11.84 g, 31.77 mmol) in CH$_3$CN (25 mL) was transferred to the LiBF$_4$ solution via cannula and more CH$_3$CN (15 mL) was used to ensure complete transfer by rinsing the Schlenk flask. The solution was stirred under nitrogen at 45-55° C. for 8 days, during which time the solution turned cloudy. The flask was periodically vented with a needle to purge (CH$_3$)$_3$SiF generated by the reaction. Volatiles were removed under vacuum to yield 6.75 g of crude white solid (90% yield). A portion of the crude product (3.25 g) was dissolved in ether (500 mL) and then washed successively with saturated Li$_2$CO$_3$(aq) (4×25 mL), water (50 mL), more saturated Li$_2$CO$_3$ (aq) (50 mL), nearly saturated LiCl (aq) (2×25 mL), and more water (2×25 mL). The ether solution was then concentrated on the rotary evaporator. The resulting solid was dried by co-evaporation with toluene (50 mL) followed by freeze-drying twice from C$_6$H$_6$ (12 mL). The dry white powder was stored inert atmosphere. Yield: 2.59 g (80% recovery). $^1$H NMR (300 MHz, DMSO-$d_6$, 22° C.): δ (ppm) 5.79 (ddt, $J_{H-H}^3$=17.1, 10.3, 6.7 Hz, 2H, CH$_2$=CHCH$_2$), 4.99 (ddt, $J_{H-H}^3$=17.2, 1.7 Hz, $J_{H-H}^2$=2.1 Hz, 2H, CH$_2$=CHCH$_2$), 4.93 (ddt, $J_{H-H}^3$=10.2, 1.1 Hz, $J_{H-H}^2$=2.2 Hz, 2H, CH$_2$=CHCH$_2$), 3.35 (t, $J_{H-H}^3$=5.5 Hz, 2H, CH(COO)$_2$B), 2.00 (dt, $J_{H-H}^3$=7.2, 6.9 Hz, 4H, CH$_2$=CHCH$_2$), 1.84-1.72 (m, 4H, CH$_2$CH(COO)$_2$B), 1.40-1.18 (m, 20H, CH$_2$=CHCH$_2$(CH$_2$)$_5$CH$_2$CH(COO)$_2$B). $^{13}$C NMR (75 MHz, DMSO-$d_6$, 22° C.): δ (ppm) 168.21, 138.84, 114.62, 47.66, 33.17, 29.01, 28.64, 28.42, 28.24, 27.00, 26.23. ESI-MS: calculated for C$_{24}$H$_{36}$BO$_8$ [M]$^-$ 463.3, found 463.2.

Example 2

ADMET Polymerization of Lithium bis(non-8-enyl-malonato)borate

Lithium bis(non-8-enyl-malonato)borate (3) monomer was polymerized by acyclic diene metathesis (ADMET) to its polymer (4) according to the following reaction sequence:

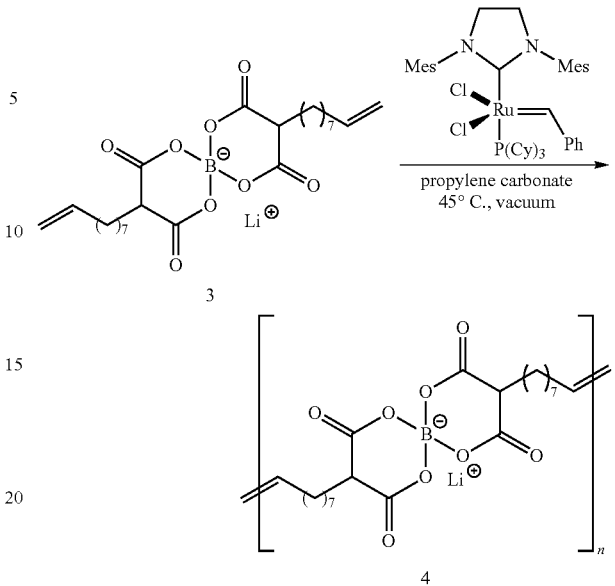

ADMET Polymerization of lithium bis(non-8-enyl-malonato)borate: An oven-dried 50 mL Schlenk tube was charged with a magnetic stirbar, 3 (0.2527 g, 0.532 mmol), and Grubbs 2$^{nd}$ generation catalyst (IMes)RuCl$_2$(=CHPh)(PCy$_3$) (3.0 mg, 3.5 µmol) under nitrogen atmosphere then capped with a septum. Using a gas-tight syringe, anhydrous propylene carbonate (1.0 mL) was added and then the septum was changed for a glass stopper under a nitrogen flush. The flask was heated to 45° C. in an oil bath and opened to vacuum for 1 h before closing the stopcock. The solution was stirred at 45° C. under static vacuum for 12 h. The flask was opened again to vacuum for 2.5 h before closing the stopcock and stirring at 45° C. under static vacuum for 48 h. The flask was back-filled with nitrogen and the glass stopper changed for a septum under a flush of nitrogen. The polymer was precipitated upon addition of anhydrous toluene (10 mL) with vigorous stirring for 4 h. The supernatant liquid was removed via syringe and replaced with fresh toluene (10 mL) followed by stirring overnight. The liquid was removed via syringe and then volatiles were removed under vacuum. The polymer was dissolved in anhydrous acetone (1.5 mL) and then, using a gas-tight syringe, the polymer solution was precipitated from vigorously stirring toluene under a nitrogen atmosphere. After stirring overnight, the supernatant liquid was removed via cannula and replaced with fresh toluene then stirred for 5 h before again removing the liquid via cannula. Volatiles were removed by stirring the solid polymer under vacuum at 22° C. for 3 h, then at 70° C. overnight, then finally at 110-120° C. for 22 h to yield a beige solid. Yield: ~0.16 g (63% yield). $^1$H NMR (300 MHz, DMSO-$d_6$, 22° C.): δ (ppm) 5.43-5.29 (m, 2H, CH$_2$CH=CHCH$_2$), 3.38-3.30 (m, 2H, CH(COO)$_2$B), 2.06-1.87 (m, 4H, CH$_2$CH=CHCH$_2$), 1.84-1.72 (m, 4H, CH$_2$CH(COO)$_2$B), 1.40-1.16 (m, 20H, CH=CHCH$_2$(CH$_2$)$_5$CH$_2$CH(COO)$_2$B). $^{13}$C NMR (125 MHz, DMSO-$d_6$, 22° C.): δ (ppm) 168.21, 168.18, 130.13, 130.05, 129.98, 129.64, 47.70, 32.04, 29.12, 29.05, 28.97, 28.90, 28.74, 28.60, 28.44, 26.99, 26.69, 26.31, 26.12, 26.00. Anal. Calcd: C, 59.75; H, 7.29; Li, 1.57. Found: C, 59.05; H, 7.16; Li, 1.49.

Figure 2:
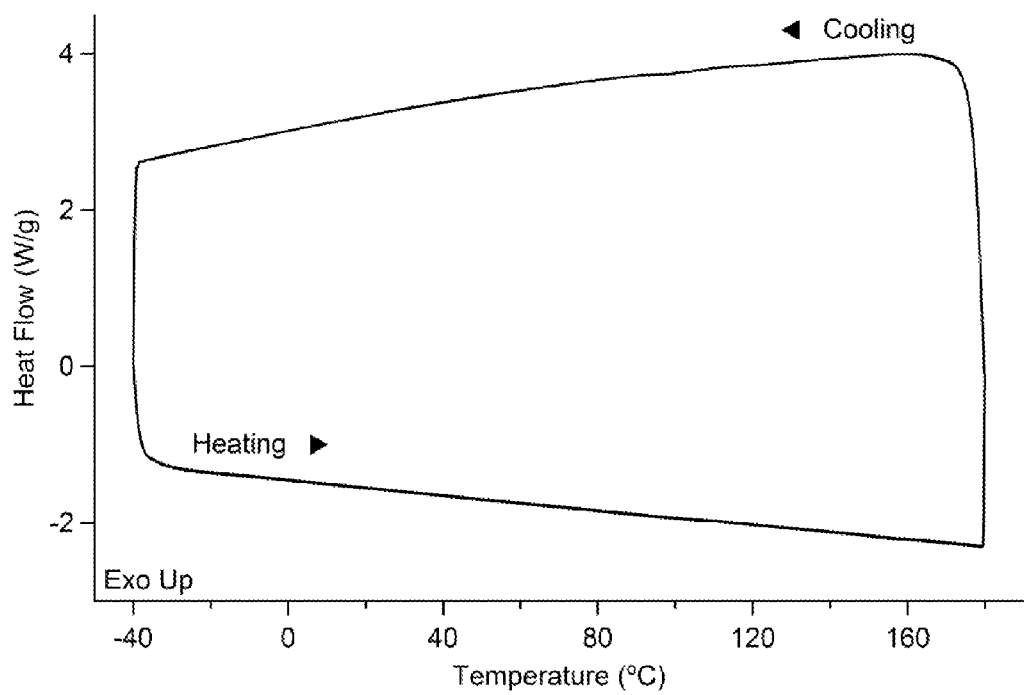
FIG. 2 shows a differential scanning calorimetry trace (second and third heating cycles) for poly(lithium bis(non-8-enyl-malonato)borate) (4) at a heating rate of 10° C./min, showing no significant thermal transitions in the range −40-180° C.

FIG. 1 shows a thermogravimetric analysis and FIG. 2 a differential scanning calorimetry trace of poly(lithium bis(non-8-enyl-malonato)borate) (4).

Example 3

Thiol-ene Polymerization of Lithium bis(non-8-enylmalonato)borate

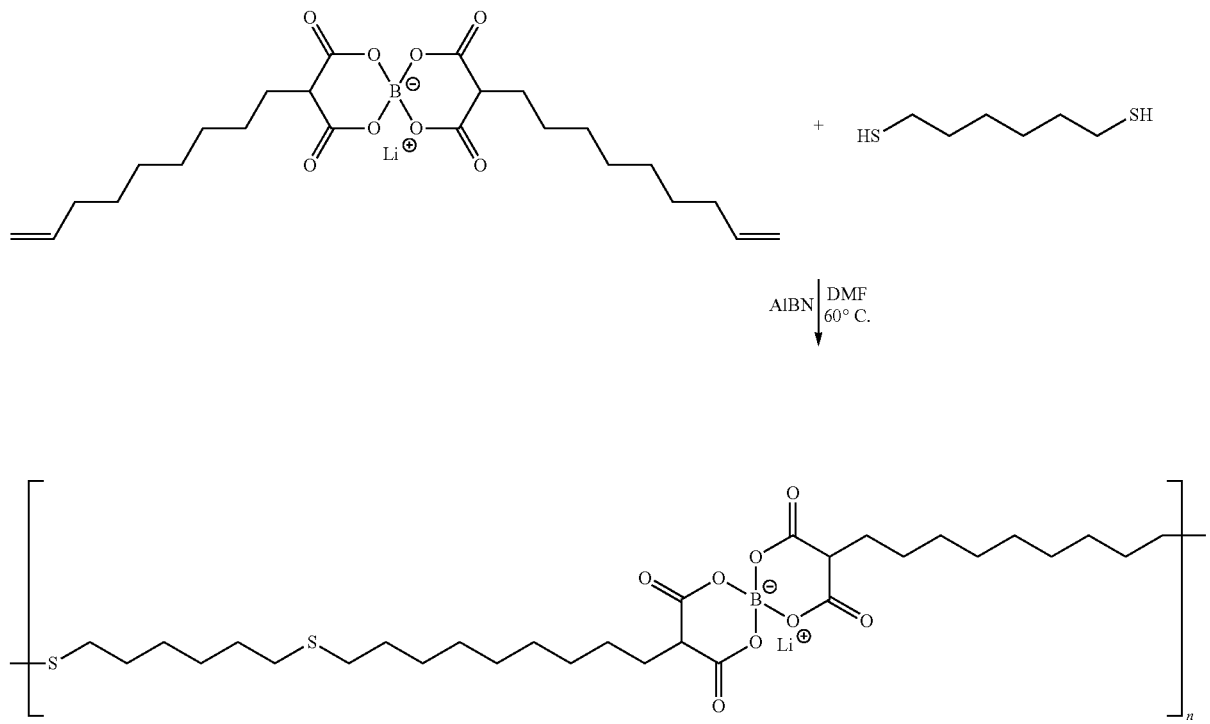

Lithium bis(non-8-enylmalonato)borate (0.202 g, 0.425 mmol), 1,6-hexanedithiol (65 μL, 0.425 mmol), azobisisobutyronitrile (AIBN) (6.8 mg, 0.041 mmol) and N,N-dimethylformamide (0.95 mL) were sealed in a 25 mL pear-shaped flask and subjected to three freeze-thaw degassing cycles, after which the contents were left under vacuum. The flask was placed in an oil bath thermostatted at 60° C. and stirred for 54 h then chilled under running water before exposure to air. The polymer was twice precipitated into stirring diethyl ether (15 mL) to yield a white solid after centrifugation and drying under vacuum. $^1$H NMR (300 MHz, DMSO-$d_6$, 22° C.): δ (ppm) 3.37-3.31 (m, 2H, CH(COO)$_2$B), 2.48-2.42 (m, 8H, SCH$_2$), 1.84-1.74 (m, 4H, CH$_2$CH(COO)$_2$B), 1.55-1.43 (m, 8H, SCH$_2$CH$_2$), 1.39-1.19 (m, SCH$_2$CH$_2$(CH$_2$)$_6$+SCH$_2$(CH$_2$)$_2$CH$_2$S). SEC (DMF+0.1 M LiBr, 40° C.) $M_{n,SEC}$=12.4 kg/mol, $M_w/M_n$=1.95 (against PEO standards),

Example 4

Thiol-Ene Gelation Polymerization of Lithium bis(non-8-enylmalonato)borate

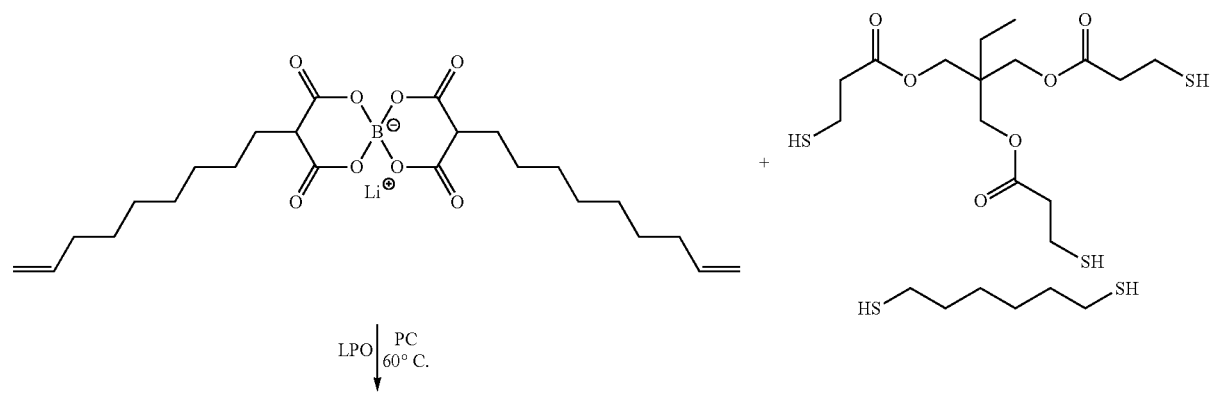

-continued

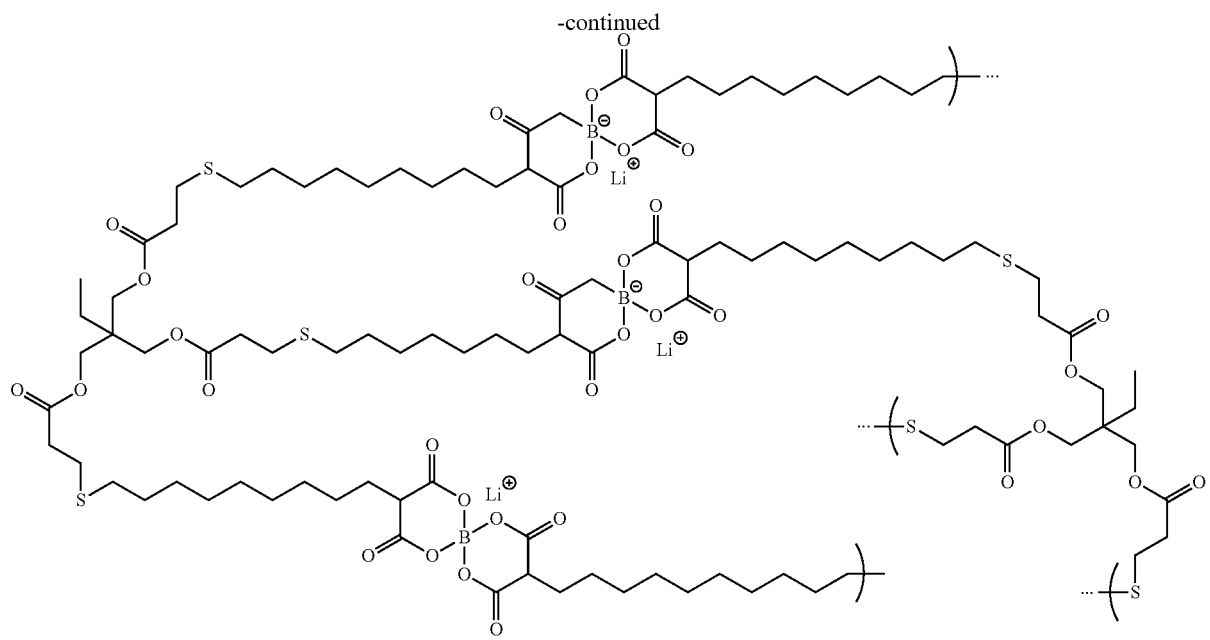

Under an argon atmosphere, lithium bis(non-8-enylmalonato)borate (0.260 g, 0.553 mmol) was mixed with 1,6-hexanedithiol (0.015 g, 0.101 mmol) and trimethylpropane tris(3-mercaptopropionate) (0.120 g, 0.302 mmol) in propylene carbonate (0.239 mL). The solution was stirred with a spatula then centrifuged to mix thoroughly. Lauroyl peroxide (4.0 mg, 0.010 mmol) was added. This solution was transferred onto a glass plate, surrounded by a 0.25 mm thick Teflon spacer, and another glass plate was placed on top of the solution. This sandwich was clamped together. The assembly was placed on top of a hot plate at 70° C. for 21 h. The plates were then separated and a free-standing gel of polymer was removed from the glass plate.

Example 5

Hydrosilation Polymerization

Under a nitrogen atmosphere, lithium bis(non-8-enylmalonato)borate (1.0 equivalent), a disilane (1.0 equivalent) and Karstedt's catalyst (0.1 equivalent) are dissolved in tetrahydrofuran (THF) and then stirred at 22° C. for 3-5 h. The resulting polymerization reaction is exposed to air and poured into rapidly stirred diethyl ether. The resulting solid is redissolved in THF and twice precipitated into stirring diethyl ether to yield a solid.

The disilanes are of the formula G-(X)$_2$:
X=—SiH(CH$_3$)$_2$ and G=O
X=—SiH(CH$_3$)$_2$ and G=—[O—Si(CH$_3$)$_2$]$_n$—O—
X=—SiH$_2$(CH$_3$) and G=—[O—Si(CH$_3$)$_2$]$_n$—O—
X=—SiH(CH$_3$)$_2$ and G=—[O—(CH$_2$CH$_2$)]$_n$—O—
X=—SiH(CH$_3$)$_2$ and G=—[(CH$_2$CH$_2$)]$_n$—

Example 6

Phosphinylation Polymerization

Under a nitrogen atmosphere, lithium bis(non-8-enylmalonato)borate (1.0 equivalent), a diphosphine (1.0 equivalent) and azobisisobutyronitrile (AIBN) (0.01 equivalent) are dissolved in N,N-dimethylformamide (DMF) and then stirred at 85° C. for 2-3 h. The resulting polymerization reaction is cooled, exposed to air, and poured into rapidly stirred diethyl ether. The polymer was twice precipitated into stirring diethyl ether to yield a solid.

The phosphines are of the formula G-(X)$_2$:
X=—PH(CH$_3$) and G=CH$_2$
X=—PH(CH$_3$) and G=—CH$_2$—[O—Si(CH$_3$)$_2$]$_n$—O—CH$_2$—
X=—PH$_2$ and G=—CH$_2$—[O—Si(CH$_3$)$_2$]$_n$—O—CH$_2$—
X=—PH(CH$_3$) and G=—[(CH$_2$CH$_2$)]$_n$—
X=—PH(CH$_3$) and G=—[(CH$_2$CH$_2$)]$_n$—
X=—PH and G=—C$_6$H$_4$-(ortho, meta, or para).

Example 7

Electrochemical Stability Measurements

Under inert atmosphere, poly(lithium bis(non-8-enyl-malonato)borate) (poly(LiBNMB)) was dissolved in dry, degassed propylene carbonate in a glass vial at a lithium ion concentration of [Li$^+$] approximately 0.2 mol/L. A platinum microelectrode (working electrode) and a lithium metal electrode (counter electrode) were submerged in the solution and cyclic voltammograms were recorded using a Gamry PCI4/300 Potentiostat/Galvanostat. Anodic sweeps start at open circuit potential (~3 V vs Li/Li$^+$) and scan at 10 mV/sec between 7 V and 2 V. Cathodic sweeps start at open circuit potential and scan at 10 mV/sec between 0.1 V and 3 V. Full sweeps start at open circuit potential and scan at 1 V/sec between 8 V and 0.1 V. The results are given in FIGS. 3 to 5.

Figure 3:
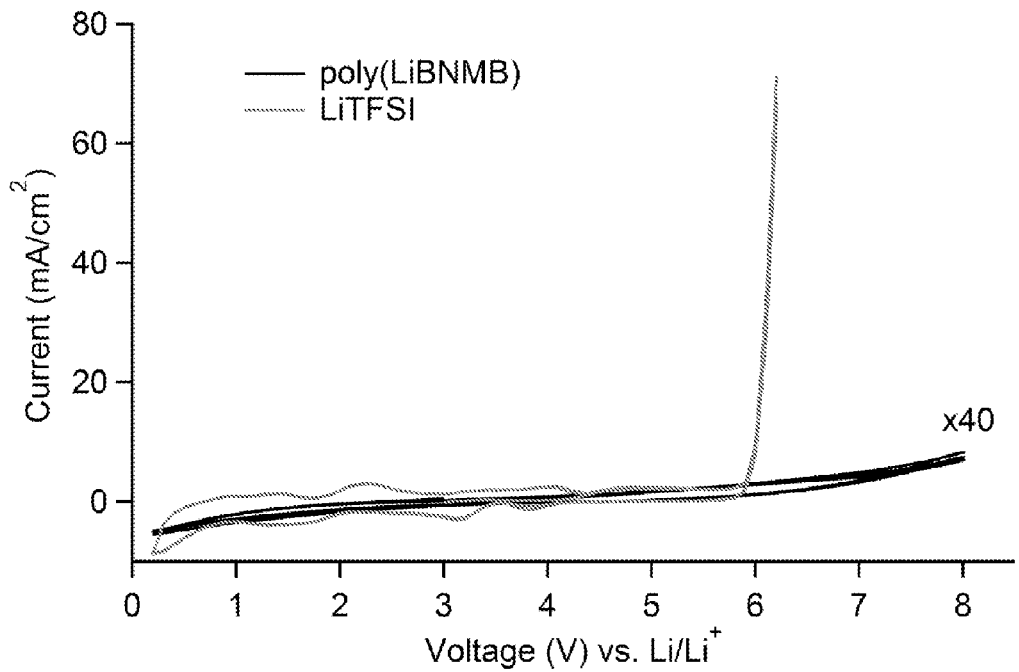
FIG. 3 shows cyclic voltammograms of poly(lithium bis(non-8-enyl-malonato)borate) (poly(LiBNMB)) (black curves) and lithium bis(trifluoromethanesulfonyl)imide (LiTFSI) (grey curves) in propylene carbonate at a lithium ion concentration [Li]=0.2 mol/L, using a fast scan rate of 1 V/sec. Note that the poly(LiBNMB) curves have been multiplied by a factor of 40 as compared to the LiTFSI curves to accentuate the shape of the curves.

FIG. 3 shows cyclic voltammograms of poly(lithium bis (non-8-enyl-malonato)borate) (poly(LiBNMB)) (black curves) and lithium bis(trifluoromethanesulfonyl)imide (LiTFSI) (grey curves) in propylene carbonate at a lithium ion concentration [Li]=0.2 mol/L, using a fast scan rate of 1 V/sec. Four cycles are shown for each compound, and the poly(LiBNMB) traces are amplified by a factor of 40 as compared to the LiTFSI traces to accentuate the shape of the curve. The upward spike in the grey curve near 6 V indicates the irreversible decomposition of LiTFSI, whereas the absence of any features in the poly(LiBNMB) indicates its electrochemical stability to 8 V.

Figure 4:
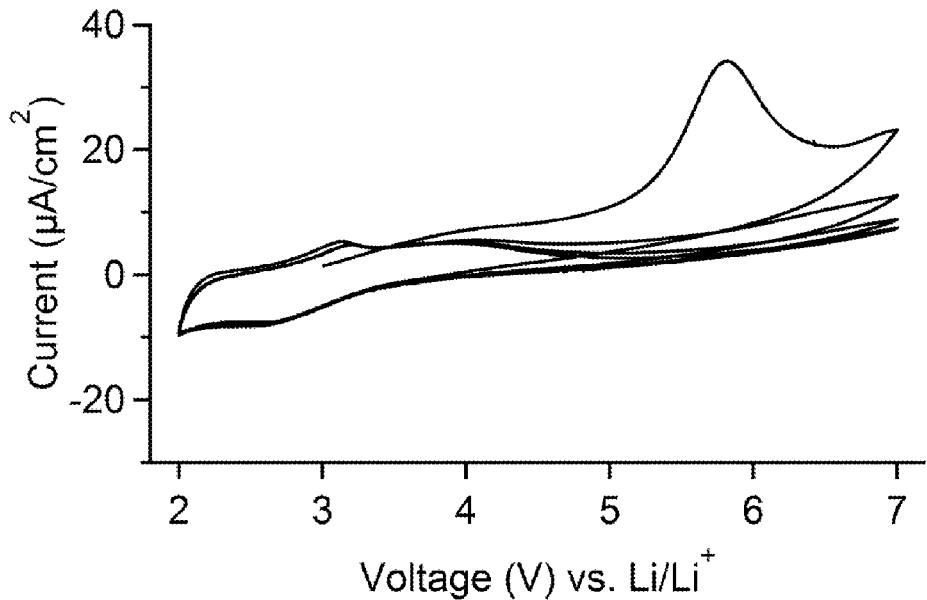
FIG. 4 shows an anodic cyclic voltammogram of poly (lithium bis(non-8-enyl-malonato)borate) (poly(LiBNMB)) in propylene carbonate at a lithium ion concentration [Li]=0.2 mol/L, using a slow scan rate of 10 mV/sec.

FIG. 4 shows an anodic cyclic voltammogram of poly (lithium bis(non-8-enyl-malonato)borate) (poly(LiBNMB)) in propylene carbonate at a lithium ion concentration [Li]=0.2 mol/L, using a slow scan rate of 10 mV/sec. Four cycles are shown for this compound, demonstrating the occurrence of a small degree of irreversible decomposition near 6 V during the first cycle. Subsequent cycles indicate that the polymer is stable at 7 V.

Figure 5:
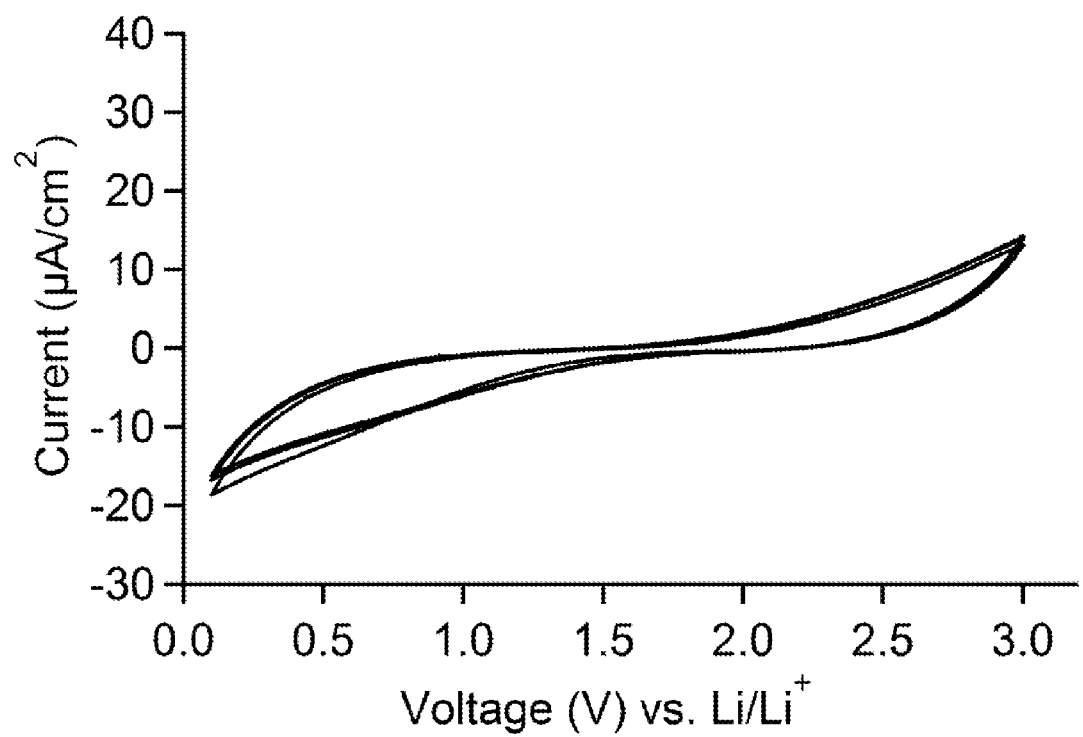
FIG. 5 shows a cathodic cyclic voltammogram of poly (lithium bis(non-8-enyl-malonato)borate) (poly(LiBNMB)) in propylene carbonate at a lithium ion concentration [Li]=0.2 mol/L, using a slow scan rate of 10 mV/sec.

FIG. 5 shows a cathodic cyclic voltammograms of poly (lithium bis(non-8-enyl-malonato)borate) (poly(LiBNMB)) in propylene carbonate at a lithium ion concentration [Li]=0.2 mol/L, using a slow scan rate of 10 mV/sec. Four cycles are shown for this compound, demonstrating that poly(LiBNMB) is electrochemically stable at voltages as low as 0.1 V.

As used herein, "hydrocarbyl" means a group containing carbon and hydrogen, and optionally further containing a heteroatom, for example, 1-10, 1-5, or 1-3 heteroatoms selected from oxygen, nitrogen, halogen, silicon, sulfur, or a combination thereof. For example, a hydrocarbyl group includes diorganosiloxanes such as dimethylsiloxanes as well as polysiloxanes, polythiophenes, poly(pyrroles), polyfurans, poly(fluorenes) and the like, optionally terminated by an alkylene group.

"Alkyl" means straight or branched chain saturated aliphatic hydrocarbyl group having the specified number of carbon atoms, a valence of one, and optionally substituted with one or more substituents where indicated. "Alkylene" means a divalent alkyl group, wherein the connecting bonds can be on the same or different carbon atoms.

"Alkenyl" means a hydrocarbon chain of either a straight or branched configuration comprising one or more unsaturated carbon-carbon bonds, which can occur in any stable point along the chain, such as ethenyl and propenyl. "Alkenylene" means a divalent alkenyl group wherein the connecting bonds can be on the same or different carbon atoms.

"Alkoxy" means an alkyl group as defined above having the indicated number of carbon atoms attached through an oxygen bridge. Examples of alkoxy include methoxy, ethoxy, n-propoxy, i-propoxy, n-butoxy, 2-butoxy, t-butoxy, n-pentyloxy, 2-pentyloxy, 3-pentyloxy, isopentyloxy, neopentyloxy, n-hexyloxy, 2-hexyloxy, 3-hexyloxy, and 3-methylpentyloxy. "Alkyleneoxy" means a divalent alkoxy group wherein the second point of attachment is to a carbon atom of the alkylene group.

"Alkylthio" means an alkyl group as defined above having the indicated number of carbon atoms attached through a sulfur bridge. "Alkylenethio" means a divalent alkylthio group wherein the second point of attachment is to a carbon atom of the alkylene group.

"Alkanoyl" means an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—. "Alkylenoyl" means a divalent alkanoyl group wherein one connecting bond is to a carbon atom of the alkylene group and one is to the carbonyl carbon.

"Alkoxycarbonyl" means an alkoxy group as defined above having the indicated number of carbon atoms, attached through a keto linkage. The carbon of the keto linker is not included in the numbering, thus a $C_2$alkoxycarbonyl has the formula $CH_3CH_2O(C=O)$—. "Alkylenoxyoyl", means a divalent alkoxycarbonyl group wherein one connecting bond is to a carbon atom of the alkylene group and one is to the carbonyl carbon.

"Aryl" means aromatic groups containing only carbon in the aromatic ring or rings. Such aromatic groups can be further substituted with carbon or non-carbon atoms or groups. Typical aryl groups contain 1 to 3 separate, fused, or pendant rings and from 6 to about 18 ring atoms, without heteroatoms as ring members. Aryl groups include, for example, phenyl, naphthyl, including 1-naphthyl and 2-naphthyl, and bi-phenyl. "Arylene" means a divalent aromatic group.

"Alkylenearylene" means an alkylene group as defined above linked to an arylene group as defined above, in any order, e.g., —$CH_2CH_2(C_6H_6)$— or —$(C_6H_6)CH_2CH_2$—. "Alkylenearylenealkylene" means an arylene group linked to two alkylene groups, in any order, e.g., —$CH_2CH_2(C_6H_6)CH_2CH_2CH_2$— or —$CH_2CH_2CH_2(C_6H_6)CH_2CH_2$—.

"Heteroaryl" means a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. Examples of heteroaryl groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline. "Heteroarylene" means a divalent heteroaryl group. "Heteroarylalkyl" means heteroaryl and alkyl as defined above, wherein the point of attachment is on the alkyl group. This term includes pyridylmethyl, thiophenylmethyl, and pyrrolyl(1-ethyl). "Heteroarylenealkyl" means a divalent heteroarylalkyl group where the second point of attachment is on the heteroarylene group.

The term "substituted" as used herein means that any one or more hydrogens on the designated atom or group is replaced with a selection from the indicated group, provided that the designated atom's normal valence is not exceeded. When a substituent is oxo (i.e., =O), then 2 hydrogens on the atom are replaced. When aromatic moieties are substituted by an oxo group, the aromatic ring is replaced by the corresponding partially unsaturated ring.

The use of the terms "a," "an," and "the" and similar referents (especially in the context of the following claims) are to be construed to cover both the singular and the plural, unless otherwise indicated herein or clearly contradicted by context. "Or" means "and/or." The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. The term "combination thereof" means a combination comprising one or more the named items optionally with one or more similar items not named.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context.

The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A metal bis(malonato) borate monomer having the Formula I

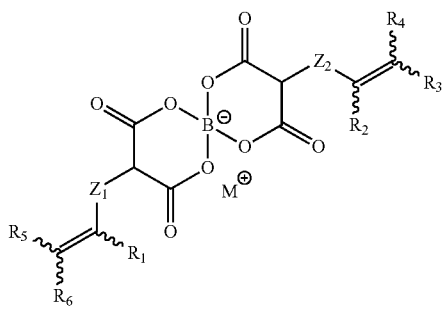

(Formula I)

wherein

M is $Li^+$, $Mg^{+2}$, $Zn^{2+}$, $Na^+$, $K^+$, $NR_4^+$ wherein R is alkyl or branched alkyl, having 1 to 4 carbon atoms, optionally substituted with cyano, chloro, fluoro, or a combination thereof;

$Z_1$ and $Z_2$ are the same or different, and are each straight-chain or branched $C_2$-$C_{30}$ alkylene, straight-chain or branched $C_2$-$C_{30}$ alkyleneoxy, straight-chain or branched $C_2$-$C_{30}$ alkylenoyl, straight-chain or branched $C_2$-$C_{30}$ alkylenoxycarbonyl, or straight-chain or branched $C_2$-$C_{30}$ alkylenethio, optionally substituted with —CN or —F; alkylenearylene having 1 to 15 carbon atoms in the alkylene group and 6 to 10 carbon atoms in the arylene group wherein the alkylenearylene is optionally substituted with 1 to 3 straight or branched chain alkyl groups having 1 to 6 carbon atoms, —CN, or —F; alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F; or arylene having 6 to 10 carbon atoms, optionally substituted with 1 to 3 straight or branched chain alkyl groups having 1 to 6 carbon atoms, —CN, or —F; and each of $R_1$, $R_2$, $R_3$, $R_4$, $R_5$ and $R_6$ are the same or different and are straight-chain alkyl having 1 to 8 carbon atoms, optionally substituted with —CN, —F, an alkenyl group having 2 to 8 carbon atoms, or aryl having 6 to 8 carbon atoms, optionally substituted with 1 to 3 straight or branched chain alkyl groups having 1 to 2 carbon atoms, —CN, or —F, and wherein each of $R_1$, $R_2$, $R_3$, $R_4$, $R_5$ and $R_6$ has 1 to 8 carbon atoms.

2. The metal bis(malonato) borate monomer of claim 1, wherein $Z_1$ and $Z_2$ are the same or different, and are each selected from straight-chain $C_2$-$C_{20}$ alkylene, straight-chain $C_2$-$C_{20}$ alkyleneoxy, straight-chain $C_2$-$C_{20}$ alkylenoyl, straight-chain $C_2$-$C_{20}$ alkylenoxycarbonyl, straight-chain $C_2$-$C_{20}$ alkylenethio, or $C_2$-$C_{18}$ arylene.

3. The metal bis(malonato) borate monomer of claim 1, wherein $Z_1$ and $Z_2$ are the same or different, and are each selected from straight-chain $C_2$-$C_{12}$ alkylene, straight-chain $C_2$-$C_{12}$ alkyleneoxy, straight-chain $C_2$-$C_{12}$ alkylenoyl, straight-chain $C_2$-$C_{12}$ alkylenoxycarbonyl, straight-chain $C_2$-$C_{12}$ alkylenethio, or $C_2$-$C_{18}$ arylene.

4. The metal bis(malonato) borate monomer of claim 1, wherein $Z_1$ and $Z_2$ are the same or different, and are selected from straight chain $C_2$-$C_{20}$ alkylene, straight chain $C_2$-$C_{20}$ alkyleneoxy, or straight chain $C_2$-$C_{20}$ alkylenethio.

5. The metal bis(malonato) borate monomer of claim 1, wherein $Z_1$ and $Z_2$ are the same or different, and are selected from straight chain alkylene, alkyleneoxy, or alkylenethio having 7 to 11 carbon atoms.

6. The metal bis(malonato) borate monomer of claim 1, wherein $R_1$ and $R_2$ are the same, and $R_3$, $R_4$, $R_5$ and $R_6$ are the same.

7. The metal bis(malonato) borate monomer of claim 1, wherein M is $Li^+$.

8. A metal bis(malonato) borate monomer having the Formula I

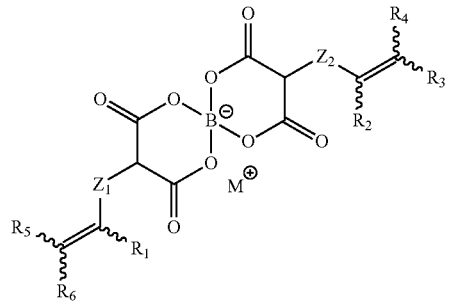

(Formula I)

wherein

M is $Li^+$, $Mg^{+2}$, $Zn^{2+}$, $Na^+$, $K^+$, $NR_4^+$ wherein R is alkyl or branched alkyl, having 1 to 4 carbon atoms, optionally substituted with cyano, chloro, fluoro, or a combination thereof;

$Z_1$ and $Z_2$ are the same or different, and are each straight-chain or branched $C_2$-$C_{30}$ alkylene, straight-chain or branched $C_2$-$C_{30}$ alkyleneoxy, straight-chain or branched $C_2$-$C_{30}$ alkylenoyl, straight-chain or branched $C_2$-$C_{30}$ alkylenoxycarbonyl, or straight-chain or branched $C_2$-$C_{30}$ alkylenethio, optionally substituted with —CN or —F; alkylenearylene having 1 to 15 carbon atoms in the alkylene group and 6 to 10 carbon atoms in the arylene group wherein the alkylenearylene is optionally substituted with 1 to 3 straight or branched chain alk groups having 1 to 6 carbon atoms —CN or —F; alkylenearylenealkylene having 1 to 15 carbon atoms in each alkylene group, wherein each alkylene group is the same or different, and 6 to 10 carbon atoms in the arylene group wherein the alkylenearylenealkylene is optionally substituted with 1 to 3 straight or branched chain alkyl groups having 1 to 6 carbon atoms, —CN, or —F; or arylene having 6 to 10 carbon atoms, optionally substituted with 1 to 3 straight or branched chain alkyl groups having 1 to 6 carbon atoms —CN or —F; and each of $R_1$, $R_2$, $R_3$, $R_4$, $R_5$ and $R_6$ are the same or different and are H, straight-chain alkyl having 1 to 8 carbon atoms, optionally substituted with —CN, —F or an alkenyl group having 2 to 8 carbon atoms or aryl having 6 to 10 carbon atoms optional substituted with 1 to 3 straight or branched chain alkyl groups having 1 to 8 carbon atoms, —CN, or —F, wherein at least one of $R_1$, $R_2$, $R_3$, $R_4$, $R_5$ and $R_6$ has 1 to 8 carbon atoms, at least one of $R_3$ and $R_4$ is hydrogen, and at least one of $R_5$ and $R_6$ is hydrogen.

9. The metal bis(malonato) borate monomer of claim 8, having the formula II

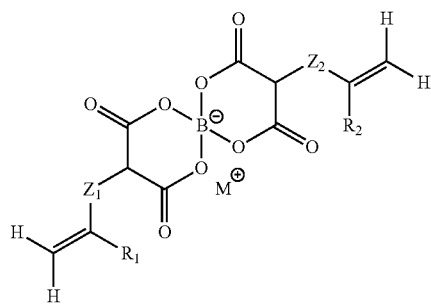

(Formula II)

wherein
M, $Z_1$, $Z_2$, $R_1$ and $R_2$ are as defined in claim 8.

10. The metal bis(malonato) borate monomer of claim 8, wherein $Z_1$ and $Z_2$ are the same or different, and are each selected from straight-chain $C_2$-$C_{20}$ alkylene, straight-chain $C_2$-$C_{20}$ alkyleneoxy, straight-chain $C_2$-$C_{20}$ alkylenoyl, straight-chain $C_2$-$C_{20}$ alkylenoxycarbonyl, straight-chain $C_2$-$C_{20}$ alkylenethio, or $C_2$-$C_{18}$ arylene.

11. The metal bis(malonato) borate monomer of claim 8, wherein $Z_1$ and $Z_2$ are the same or different, and are each selected from straight-chain $C_2$-$C_{12}$ alkylene, straight-chain $C_2$-$C_{12}$ alkyleneoxy, straight-chain $C_2$-$C_{12}$ alkylenoyl, straight-chain $C_2$-$C_{12}$ alkylenoxycarbonyl, straight-chain $C_2$-$C_{12}$ alkylenethio, or $C_2$-$C_{18}$ arylene.

12. The metal bis(malonato) borate monomer of claim 8, wherein $Z_1$ and $Z_2$ are the same or different, and are selected from straight chain $C_2$-$C_{20}$ alkylene, straight chain $C_2$-$C_{20}$ alkyleneoxy, or straight chain $C_2$-$C_{20}$ alkylenethio.

13. The metal bis(malonato) borate monomer of claim 8, wherein $Z_1$ and $Z_2$ are the same or different, and are selected from straight chain alkylene, alkyleneoxy, or alkylenethio having 7 to 11 carbon atoms.

14. The metal bis(malonato) borate monomer of claim 8, wherein M is $Li^+$.

* * * * *